United States Patent [19]
Akhavan-Tafti

[11] Patent Number: 6,001,614
[45] Date of Patent: *Dec. 14, 1999

[54] METHODS OF SYNTHESIZING LABELED POLYNUCLEOTIDES BY LIGATION OF MULTIPLE OLIGOMERS

[75] Inventor: Hashem Akhavan-Tafti, Howell, Mich.

[73] Assignee: Lumigen, Inc., Southfield, Mich.

[*] Notice: This patent is subject to a terminal disclaimer.

[21] Appl. No.: 09/241,353

[22] Filed: Feb. 2, 1999

Related U.S. Application Data

[63] Continuation of application No. 09/121,887, Jul. 24, 1998.
[51] Int. Cl.$^6$ .............................. C12P 19/34; C12Q 1/68; C07H 21/04
[52] U.S. Cl. ........................... 435/91.5; 435/6; 435/91.2; 435/91.52; 536/25.3; 536/25.32
[58] Field of Search ............................... 536/25.3, 25.32; 435/6, 91.1, 91.2, 91.5, 91.52

[56] References Cited

U.S. PATENT DOCUMENTS

| | | | |
|---|---|---|---|
| 5,403,708 | 4/1995 | Brennan | 435/6 |
| 5,478,724 | 12/1995 | Morse | 435/5 |
| 5,663,062 | 9/1997 | Sorge | 435/91.1 |
| 5,695,933 | 12/1997 | Schalling | 435/91.52 |
| 5,750,341 | 5/1998 | Macevicz | 435/6 |
| 5,770,367 | 6/1998 | Southern | 435/6 |
| 5,888,731 | 3/1999 | Yager | 435/6 |

FOREIGN PATENT DOCUMENTS 88311741   6/1989   European Pat. Off. .

OTHER PUBLICATIONS

S. Dubiley,E.Kirilov,Y.Lysov,A.Mirzabekov Nucl.Acids Res., 25, 2259–2265 (1997).
R.Handley,H.Akhavan–Tafti,A.P.Schaap, J.Clin. Ligand Assay, 20(4) 302–312 (1997).
K.D.James,A.D.Ellington, Chemistry & Biology 4, 595–605 (1997).
T.Kaczorowski,W.Szybalski, Gene 179, 189–193 (1996).
L.E.Kotler,D.Zevin–Sonkin,I.A.Sobolev,A.D.Beskin L.E.Ulanovsky,Proc.Natl.Acad.Sci.USA, 90, 4241–4245 (1993).
T.Li,K.C.Nicolaou,Nature,369,218–221 (1994).
C.E.Pritchard,E.M.Southern,Nucl.Acids Res., 25, 3403–3407 (1997).
D.Sievers,G.Von Kiedrowski, Nature, 369, 221–224 (1994).
W.Stemmer,A.Crameri,K.D.Ha,T.M.Brennan,H.L. Heyneker, Gene, 164, 49–53 (1995).
D.Y.Wu,R.B.Wallace,Genomics,4,560–569 (1989).

*Primary Examiner*—Carla J. Myers
*Assistant Examiner*—Diana Johannsen
*Attorney, Agent, or Firm*—Richard S. Handley

[57] ABSTRACT

Methods of synthesizing polynucleotides are disclosed involving the simultaneous ligation of a set of oligomer 5'-phosphates onto a template-bound primer. The set of these oligomers can be preselected to contain oligomers which are complementary to the template strand or the oligomers can be supplied as a library and allowed to self select. The synthesis by ligation can proceed unidirectionally or bidirectionally from the primer and can be used to synthesize both strands simultaneously by the use of two primers. The ligation is preferably performed with a ligase enzyme. The methods of synthesis are useful in a variety of applications, including cloning, amplification, labeling, diagnostic assays, mutation analysis and screening, gene expression monitoring and sequence analysis.

23 Claims, 6 Drawing Sheets

Branched DNA

METHODS OF SYNTHESIZING LABELED POLYNUCLEOTIDES BY LIGATION OF MULTIPLE OLIGOMERS

This application is a continuation of copending application(s) application Ser. No. 09/121,887 filed on Jul. 24, 1998.

FIELD OF THE INVENTION

The present invention relates generally to methods of synthesizing polynucleotides. More specifically, the invention relates to methods of synthesizing polynucleotides by ligation of a plurality of oligomeric units onto a template-bound primer. The plurality of oligomers can be preselected to contain oligomers which are complementary to the template strand or the oligomers can be supplied as a library and allowed to self select. The synthesis by ligation can proceed unidirectionally or bidirectionally from the primer and can be used to synthesize both strands simultaneously by the use of two primers. Amplification can be performed linearly or exponentially and can be used to copy DNA and RNA. The methods of the invention are useful in a variety of applications, including cloning, preparing labeled polynucleotides for diagnostic use, mutation analysis and screening, gene expression monitoring and sequence analysis.

BACKGROUND OF THE INVENTION

The enzymatic ligation of pairs of oligonucleotides bound to a target nucleic acid is widely known. It is generally thought that the oligomers must each be of a minimum length to be ligated efficiently. Recent work has shown this minimum length to be about 6–8 bases (C. E. Pritchard and E. M. Southern, *Nucl. Acids Res.*, 25, 3403–3407 (1997)). It is generally thought that ligation of oligonucleotides shorter than about 6 bases is not possible.

Under certain conditions, primer independent ligation can be accomplished using oligomers of at least six bases long. In this manner, PCR primers were prepared in situ from concatenated groups of a small number hexamers, heptamers or octamers (T. Kaczorowski and W. Szybalski, *Gene*, 179, 189–193 (1996); L. E. Kotler, D. Zevin-Sonkin, I. A. Sobolev, A. D. Beskin and L. E. Ulanovsky, *Proc. Natl. Acad. Sci. USA*, 90, 4241–4245 (1993)). Such ligation in the absence of a primer is undesirable in the present methods and must be avoided. The success in replicating a polynucleotide sequence in a controlled and defined manner rests in knowing the point of origination of the newly synthesized strand.

Nucleic acids can be synthesized from a template, primer and nucleotide triphosphates (NTPs) by the action of a polymerase action. Labels can be incorporated by substituting a percentage of labeled NTPs. The ability to achieve a high degree of label incorporation is limited and the precise spacing of labels is not controllable.

The polymerase chain reaction (PCR) is a method of amplifying the amount of a polynucleotide by the use of a primer complementary to each strand which span the region to be replicated. Nucleic acid synthesis proceeds by extension of each primer with a polymerase and the four dNTPs. Thermal cycling allows multiple copies of the template to be synthesized, approximately doubling the quantity of amplicon in each cycle. A variant termed Ligase Chain Reaction (LCR) involves the ligation of two pairs of oligonucleotides with a ligase enzyme to replicate the sequence of interest (D. Y. Wu and R. B. Wallace, *Genomics*, 4, 560–569 (1989)). The two oligonucleotides to be ligated constitute the entire length of the strand. Ligation of a large number of small oligomers to a primer to replicate a nucleic acid has not been achieved to the best of Applicant's knowledge.

Methods of providing sequence information using oligonucleotide ligation are disclosed in U.S. Pat. No. 5,750,341 and U.S. Pat. No. 5,770,367 and a publication (S. Dubiley, E. Kirilov, Y. Lysov and A Mirzabekov, *Nucl. Acids Res.*, 25, 2259–2265 (1997)). The reported methods differ fundamentally from those of the present invention in requiring that oligomers be ligated one at a time and the sequence be analyzed after each step. These methods are therefore far more laborious than those of the present invention.

Methods of Labeling Nucleic Acids—Present methods of labeling nucleic acids or oligonucleotides include the tailing method, random primed labeling, nick translation, the labeled branched DNA and end labeling using a labeled primer. Each method suffers disadvantages in certain applications. Use of an end labeled primer extended by PCR with unlabeled bases leads to only one or a few labels per product nucleic acid.

The tailing method incorporates an indeterminate and uncontrolled number of labels by appending a tail of non-complementary bases onto the nucleic acid of interest. This adds many additional bases, which not only adds expense, but may interfere with hybridization and lead to nonspecific binding. In addition it is not readily applicable to the synthesis of short nucleic acids or oligonucleotides since the length of the tail could exceed the length of the sequence of interest.

The random prime method, applicable to the labeling of long nucleic acids, uses a mixture of primers which are extended by a polymerase with a mixture of labeled and unlabeled bases. The number of bases which can be incorporated is variable and arbitrary in number. A mixture of numerous nucleic acid fragments of varying lengths are produced from both strands. Similarly, nick translation produces a mixture of numerous nucleic acid fragments of varying lengths from both strands. Breaks in both strands of DNA are created and new nucleic acid strands are synthesized from the position of the nick using a mix of labeled and unlabeled bases. Since the position of nicking is arbitrary, label incorporation is not controlled either.

The branched DNA technology has been used in diagnostic tests as a means to attach several labels to a target DNA. The methodology relies on the creation of several branches of synthetic nucleic acid each bound to a probe, followed by hybridization of multiple labeled oligonucleotides to each of the branched amplification multimers. The method requires the costly preparation of many probes and branched DNA and is not generally applicable, especially for the generation of short pieces of highly labeled DNA.

SUMMARY OF THE INVENTION

It is an object of the present invention to provide methods of synthesizing single or double stranded polynucleotides. It is another object of the present invention to provide methods of synthesizing polynucleotides by ligating a plurality of oligonucleotide 5'-phosphates to a primer hybridized to a template polynucleotide. It is another object of the present invention to provide methods of synthesizing polynucleotides using a library of oligonucleotide 5'-phosphates. It is another object of the present invention to provide methods of synthesizing labeled polynucleotides with a specified position and degree of label incorporation. Another object of the present invention is to provide methods for amplifying the amount of a nucleic acid by primer-directed ligation. Another object of the present invention is to provide methods for the detection of genes and the analysis of gene expression. Yet another object of the present invention is to provide methods for the detection of genetic mutations. Still another object of the present invention is to provide methods for the analysis of the base sequence of a nucleic acid.

GENERAL DESCRIPTION

It has been discovered that a series of short oligonucleotide-5'-phosphates can be simultaneously ligated onto a template-bound primer in a contiguous manner to produce the complementary strand of a template polynucleotide or nucleic acid. The nucleic acid produced can be either labeled or unlabeled by using either labeled or unlabeled short oligomers. The oligomers in the set each preferably contain the same number of bases. When a sequence to be synthesized is known exactly, a set containing the minimum number of oligomers can be used. The oligomers are ligated in the correct order starting from the primer, to produce the correct sequence. Primer-independent ligation does not occur when using oligonucleotides of length≦5 bases. When the sequence to be synthesized is not known, a library of a large number of the total possible pool of oligomers is used. The latter situation occurs in sequence analysis and mutation screening. Ligations are preferably conducted by means of a ligase enzyme. Known chemical agents for ligating nucleotides and oligonucleotides can be employed as well.

DETAILED DESCRIPTION OF THE INVENTION

Definitions

Figure 1:
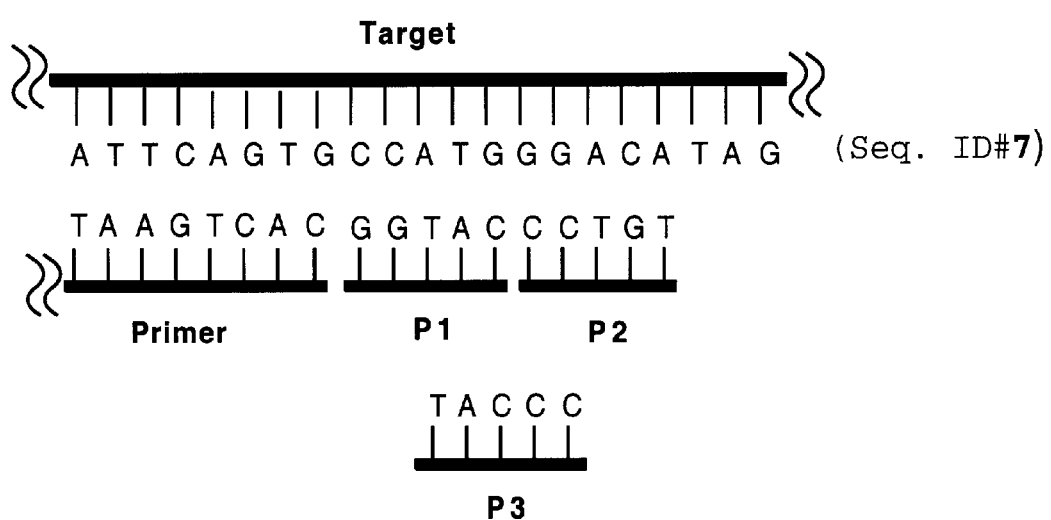
FIG. 1 schematically depicts the ligation of two oligomers P1 and P2 onto a template-bound primer in the presence of a competing nonligatable complementary oligomer P3.

Oligomer, oligonucleotide—as used herein will refer to a compound containing a phosphodiester internucleotide linkage and a 5'-terminal monophosphate group. The nucleotides can be the normally occurring ribonucleotides A, C, G, and U or deoxyribonucleotides, dA, dC, dG and dT.

Primer or probe/primer—refers to an oligonucleotide used to direct the site of ligation and is required to initiate the ligation process. Primers are of a length sufficient to hybridize stably to the template and represent a unique sequence in the template. Primers will usually be about 15–30 bases in length although longer primers can be used. Labeled primers containing detectable labels or labels which allow solid phase capture are within the scope of the term as used herein. Primer also contemplates contiguously stacked oligomers of at least six bases as is known in the art (T. Kaczorowski and W. Szybalski, *Gene*, 179, 189–193 (1996)).

Template, test polynucleotide, target are used interchangeably and refer to the nucleic acid whose length is to be replicated.

Sample—A fluid containing or suspected of containing one or more analytes to be assayed. Typical samples which are analyzed by the chemiluminescent reaction method are biological samples including body fluids such as blood, plasma, serum, urine, semen, saliva, cell lysates, tissue extracts and the like. Other types of samples include food samples and environmental samples such as soil or water.

Short oligonucleotide—As used herein, a oligonucleotide 5'-phosphate of at lest two and up to about 10 base length. The bases can be ribonucleotides or deoxyribonucleotides or analogs thereof. The length of a short oligonucleotide useful in a given context can vary within this range and may be less than the whole range. The preferred length varies depending on the particular application.

Specific binding pair—Two substances which exhibit a mutual binding affinity. Examples include antigen-antibody, hapten-antibody or antibody-antibody pairs, complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody and metal complex-ligand.

One object of the invention therefore is method for synthesizing a strand of a nucleic acid complementary to at least a portion of a target single stranded nucleic acid template comprising:

a) providing a primer which is complementary to a portion of the target single stranded nucleic acid template;

b) hybridizing the primer with the template to form a primer-template hybrid having a single stranded region and a double stranded region;

c) contacting the primer-template hybrid with a plurality of oligonucleotide 5'-monophosphates;

d) ligating to the primer-template hybrid in sequence at least some of the plurality of oligonucleotide 5'-monophosphates to extend the double stranded region and thereby synthesize a nucleic acid strand which is complementary to the portion of the template.

A preferred method of ligation uses a ligase such as a DNA ligase. Representative ligases include T4 ligase, T7 ligase, Tth ligase, Taq ligase and *E. coli* DNA ligase. The ligase can be a thermostable ligase, in which case thermal cycling techniques as discussed below are possible. Thermal cycling with a thermostable ligase is useful in methods of amplifying nucleic acids in a manner analogous to the polymerase chain reaction, but using oligomers and a ligase in place of dNTPs and a polymerase. Methods of performing enzymatic ligation reactions are generally described in e.g., Sambrook, et al., Molecular Cloning: A Laboratory Manual, 2nd Ed., Cold Spring Harbor Laboratory, New York, 1989.

Enzymatic ligation reactions are generally performed in a buffer solution, optionally in the presence of additives to promote hybridization. The buffer has a pH typically in the range of 6–9, more usually 7–8.5 and preferably in the range 7.5–8. Buffers capable of maintaining a pH in this range are suitable. The reaction can be performed over a range of temperatures in the range of 0 to about 50° C. Optimal temperatures will vary over the range depending on the nature and size of oligonucleotide phosphates to be ligated, the enzyme, presence and amount of additive and can be optimized empirically with reference to the general literature on ligases and by reference to the specific examples below. The length of time for performing the ligation can be as short as a few minutes up to several hours, although it is desirable to conduct the reaction as rapidly as possible. Single stranded DNA binding proteins can be added to oligonucleotide ligation reactions to improve their efficiency. Their effect is due to their relaxation of any secondary structure that is in the template strand thus allowing the complementary oligonucleotides to bind and ligate. *E. coli* single stranded binding protein (Promega, Madison, Wis. or Amersham/USB) and T4 Gene 32 protein (Boehringer Mannheim, Indianapolis, Ind.) can be used. The use of volume excluding agents such as polyethylene glycols (PEG) may be advantageous in promoting ligations. Inclusion of up to 200 mM NaCl may also be useful for promoting ligations. The use of other additives in enzymatic ligations is contemplated and is within the scope of the present methods. Additives include phosphate transfer agents such as ATP, sulfhydryl reagents, including DTT and 2-mercaptoethanol, and divalent cations such as $Mg^{+2}$ salts.

Ligation of oligomer 5'-phosphates also comprehends nonenzymatic methods of ligation as well. Chemical reagents which effect the formation of the phosphodiester internucleotide bond are known (CNBr: K. D. James, A. D. Ellington, *Chemistry & Biology*, 4,595,605, (1997); N-cyanoimidazole: T. Li, K. C. Nicalaou, *Nature*, 369, 218–221 (1994); EDAC: D. Sievers, G. Von Kiedrowski, *Nature*, 369, 221–224 (1994)). Chemical ligation methods have not been applied to methods of sequence analysis.

Incorporation of mismatched oligomers can occur as in other techniques, especially when the sequence has a high G-C content. The occurrence of mismatches is controllable as is the case with other hybridization methods. Temperature, salt concentration, and additives can all be employed in art-recognized manners to control the stringency of the hybridization process. Since the effect of a mismatch on a small oligomer should be proportionately greater than on a larger one, discrimination of improper sequences may show improvement over other ligation techniques.

Another embodiment uses a library of possible sequences to achieve the ligation of a series of short oligomers of length n bases to synthesize a complementary nucleic acid. The library contains many more possible combinations of the n bases (n-mers) than are required to form the product nucleic acid. When n=5, for example, there are $4^5$ or 1024 possible 5-mers which contain the four naturally occurring bases A, C, G, T and U. The library can contain all $4^n$ possible oligomers or less than the full set, but should contain at least a substantial proportion (>50%, and preferably>75%, most preferably>90%) of the possible oligomers.

Known methods of synthesizing polynucleotides, by polymerase extensions with dntps or ligation of preformed oligonucleotides, function by providing only a small number of different reactants for incorporation into the product molecule. Known ligation-based methods usually preselect the one oligonucleotide with the correct sequence. Polymerase extension methods supply the four individual bases for incorporation. The present methods differ fundamentally in providing a large number of potential reactants into the reaction mixture. Moreover, a significant number of the short oligonucleotides have a sequence appropriate for hybridization to the target but, if hybridized, would block or prematurely terminate the ligation process.

As seen in FIG. 1, oligomer P3 is complementary to a portion of the target sequence, but, if hybridized, would block ligation of P1 and P2 to the primer. Surprisingly, the presence of complementary oligomers which can not be ligated onto the primer does not interfere with or prevent the successful ligation of the desired oligomers to the template-bound primer.

The library also will contain a majority of oligonucleotide sequences which are not complementary to the target or only partially complementary. This excess of oligonucleotides, in effect, competes with the correct sequences for recognition and ligation. Nevertheless, ligation of short oligonucleotides in the correct order does occur effectively in spite of the statistical unlikelihood. The ability to faithfully replicate a nucleic acid by successive ligation of many short oligonucleotides in one step is unexpected and greatly simplifies the process compared to others known in the art.

The length of oligonucleotides to use in the present methods is governed by the interplay of several competing factors. Larger oligomers will hybridize more strongly under a given set of conditions (salt concentration, temperature) and can therefore hybridize at a higher temperature. As the length of the oligonucleotide increases, the number of discrete compounds required to assemble the complete library of all possible n-mers increases by a factor of 4 for each unit increase of n.

| Length of Oligomer | Total # of Seqences |
|---|---|
| 1 | 4 |
| 2 | 16 |
| 3 | 64 |
| 4 | 256 |
| 5 | 1024 |
| 6 | 4096 |
| 7 | 16,384 |
| 8 | 65,536 |
| 9 | 262,144 |
| 10 | 1,048,576 |

Shorter oligomers require less compounds to construct the entire library, but become more difficult, e.g. lower temperature, to hybridize and ligate as their length decreases. This, in turn, translates to greater stringency at a given temperature. Still another factor is the ability of the oligonucleotide to hybridize and initiate extension at a site not associated with the primer. Primer-independent hybridization has been demonstrated to occur, under the right conditions, with oligonucleotides as small as 6 bases. Ligation of 2 or more contiguous hexamers to produce e.g., a dodecamer or octadecamer, then effectively produces a new primer. If this happens, the ability to control the starting point for polynucleotide synthesis is compromised. On the other hand, the probability of finding multiple occurrences of a given sequence in a nucleic acid of hundreds of bases increases substantially as shorter oligonucleotides are used. In applications involving sequence determination, it is desirable to avoid or minimize the occurrence of duplicate sequence elements. The selection of the optimum length oligonucleotide to use is a compromise among these conflicting effects. The optimum length will be different in different end uses.

In practice it may not be necessary to use the full library of oligonucleotides of length n. When the number of oligonucleotides required to produce the given sequence is small compared to the total number of oligonucleotides in the library, partial libraries can be used and still maintain a high probability that all of the required oligonucleotides will be present. In some instances it may be desirable to exclude certain sequence oligonucleotides which hybridize too weakly or strongly.

It is not necessary in the present methods, except as explicitly noted below, that each component of the set of oligonucleotide 5'-phosphates used in a given method be of the same number of bases. It can be advantageous in some embodiments to use a combination of oligomers of two or more different lengths, such as pentamers and hexamers, in order to avoid the occurrence of duplicate oligomers.

In another embodiment, template-directed ligation of a plurality of a set of short oligonucleotides of the same length onto a primer can be performed in a manner which controls the endpoint of the ligation by the use of nonextendable oligomers. A nonextendable oligomer can contain the same or a different number of bases as the other oligomers in the set. The nonextendable oligomer contains a 5'-phosphate so that it can be ligated, but lacks the 3'-OH group. It could, for example, have a dideoxy base at the 3'-end of the oligomer so that there is no 3'-OH for ligation. Another type of nonextendable oligomer contains a blocked 3'-OH group for example where the hydroxyl group is blocked with a methyl group or a phosphate group, to prevent subsequent ligation. Modifications to the terminal base which prevent ligation are another possible type of nonextendable oligomer. The nonextendable oligomer can be labeled or unlabeled, depending on the need. A preferred embodiment is to use oligomers containing a dideoxy base at the 3'-terminus.

Another aspect of the present invention is a method for synthesizing a nucleic acid by ligation of a plurality of oligonucleotide 5'-phosphates onto a template-bound primer in both the 5'→3' and 3'→5' direction at the same time. This process can be performed, for example, by providing a 5'-phosphate group on the primer. Ligation can occur simultaneously from both termini of the primer as long as the appropriate ligatable oligomers are provided. The point of termination of synthesis in either or both directions can be controlled by the use of nonextendable oligomers or by excluding selected oligomers. A nonextendable oligomer for terminating synthesis in the 3'→5' direction would not have the 5'-phosphate group.

Figure 2:
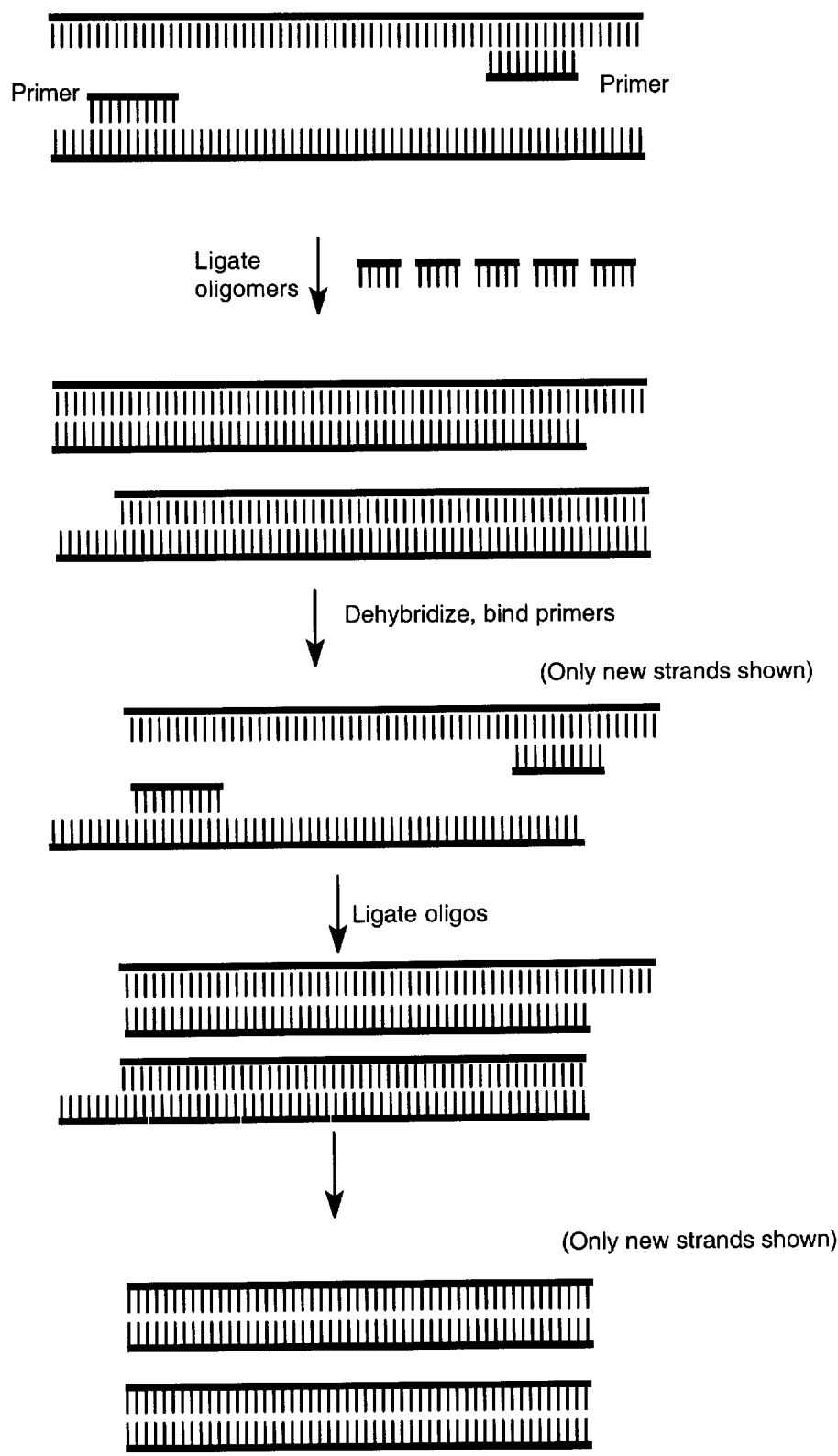
FIG. 2 schematically depicts a method for amplifying the amount of a nucleic acid using template-bound primer directed ligation of multiple oligomers. Synthesis is shown occurring in one direction in each strand, but can also be accomplished bidirectionally as described below.
Figure 3:
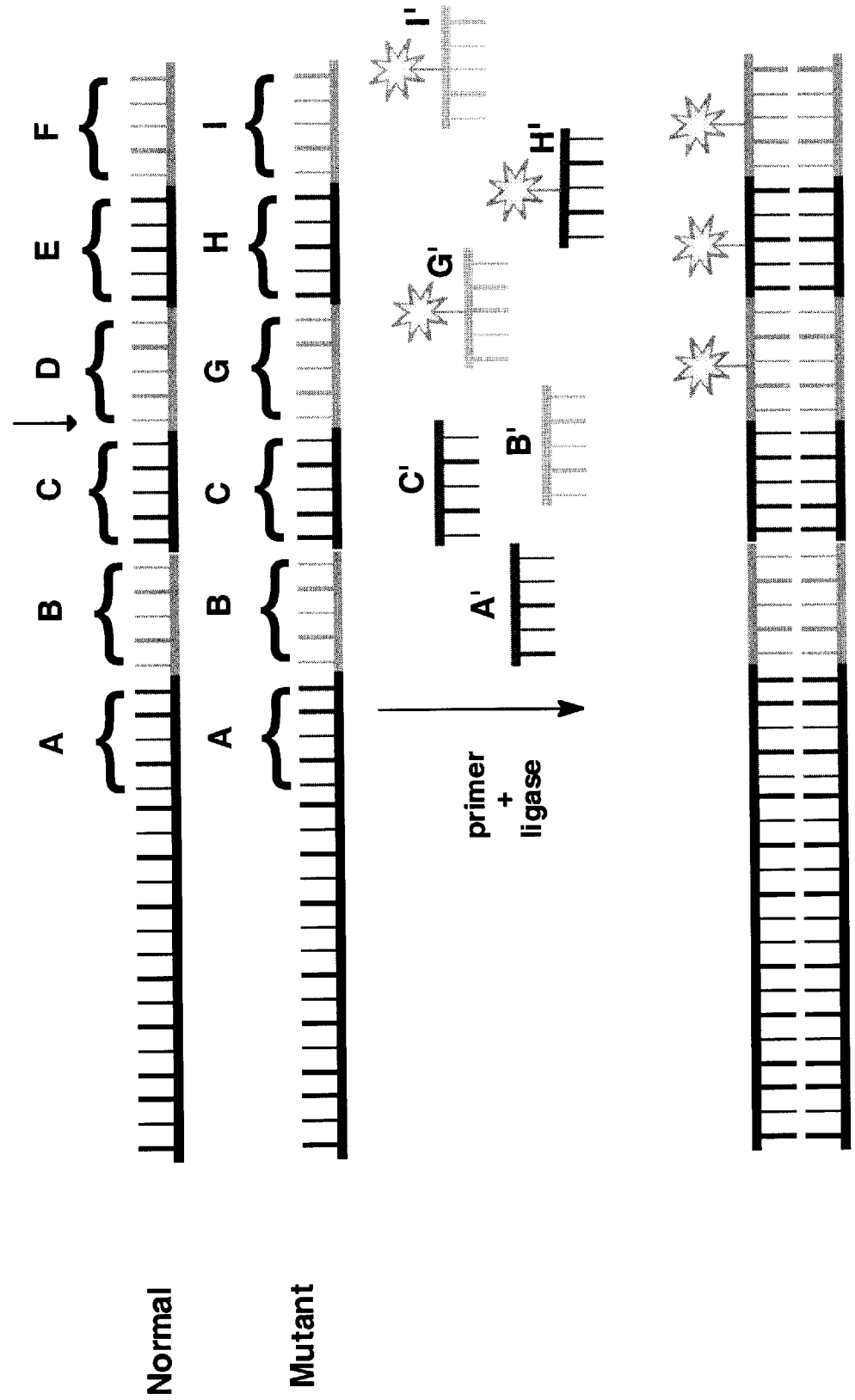
FIG. 3 schematically depicts a method for detecting a point mutation in a gene by the ligation of detectably labeled mutation specific oligomers onto a template-bound primer.

The template-directed ligation of a plurality of a set of short oligonucleotides onto a primer can be used in a method of amplifying the quantity of a target DNA. Accordingly, another aspect of the invention comprises a method of amplifying a target nucleic acid using a ligase, two primers and a set of short oligonucleotides where the probes are complementary to regions on opposing strands spanning the region of the target to be amplified. At a minimum, the oligomer set supplied for reaction must contain those oligomers required to extend both primers on their respective strands as far as the position corresponding to the 5' end of the other primer. Additional oligomers can be included, for example as would occur when using the entire library of oligomers instead of preselecting the set of oligomers. The process, shown schematically in FIG. 2, is distinct from the polymerase chain reaction, PCR, but using a library of oligomers and a ligase instead of the four deoxyribonucleotides and a polymerase. Each cycle of annealing, ligase extension and dehybridization results in a two-fold amplification of the target sequence. Since heating is generally required for separating the newly synthesized duplex nucleic acid, additional ligase may need to be added in subsequent rounds of ligation-extension. Alternatively, the process can be performed with a thermostable ligase. Thermal cycling can then be performed without replacing the ligase every cycle.

In accordance with the above description there is provided a method for amplifying the amount of a portion of a double stranded nucleic acid having a first strand and a second strand comprising:

a) providing a first primer which is complementary to a region of the first strand and a second primer which is complementary to a region of the second strand wherein the first and second regions define the portion of the double stranded nucleic acid to be amplified;

b) providing a plurality of oligonucleotide 5'-monophosphates;

c) separating the first and second strands of the double stranded nucleic acid;

d) hybridizing the first and second primers with the separated strands;

e) ligating onto the hybridized first and second primers in sequence at least some of the plurality of oligonucleotide 5'-monophosphates to extend the double stranded region and thereby synthesize a nucleic acid strand which is complementary to the portion of the template; and f) repeating steps c–e as many times as desired to increase the amount of the amplified portion of double stranded nucleic acid.

In a preferred embodiment of an amplification process, the set of oligomers is preselected to contain only those oligomers necessary to replicate the two strands, i.e. those oligomers occurring on the two strands in the region spanned by the two primers. In another preferred embodiment, nonextendable oligomers are used for the terminal positions of each strand. These two terminating oligomers, by definition, have a base sequence complementary to the first group of bases of the length of the oligomer at the 5' end of each primer.

Amplification methods in accordance with the present invention can be achieved by synthesis of each strand in both the 5'→3' and 3'→5' direction at the same time. This bidirectional amplification process can be performed, for example, by providing a 5'-phosphate group on the primer. Ligation can occur simultaneously from both termini of each primer as long as the appropriate ligatable oligomers are provided. The point of termination of synthesis in either or both directions can be controlled by the use of nonextendable oligomers or by excluding selected oligomers as described above.

As is the case with other uses of the present oligomer ligation method of synthesizing nucleic acid, either labeled or unlabeled oligomers can be used. The set of oligomers used can be the entire library, a substantial portion of the library or a preselected subset if the sequence to be amplified is known in advance.

In another aspect, the method of synthesizing specific nucleic acid sequences by ligating oligomers onto target bound primers can be used in diagnostic applications. Specific sequences characteristic of the target of interest can be detected using labeled oligomers in the method of synthesizing the new strand. When the base sequence of the target nucleic acid region is known, the corresponding oligomers needed to complete this sequence are used, at least some of which should carry a detectable label. Such methods have use in many areas of nucleic acid diagnostics, including detection of infectious agents such as *C. trachomatis* and *N. gonorrhoeae, P. carinii, M. tuberculosis,* detection of food borne pathogens such as *Salmonella* and *E. coli,* methods of detecting the expression of genes in high throughput screening assays, methods of detecting genetic abnormalities, forensic testing of DNA samples from suspected criminals, identity matching of human remains and paternity testing.

In the area of genetic abnormality testing, one application is a method for the detection of genetic mutations. The mutations can be a point mutation (a and β-Thalassemia), a single base substitution (Sickle Cell Anemia), a deletion (Cystic Fibrosis $\Delta F_{508}$, Tay-Sachs), an insertion, a duplication, a transposition of bases or a combination of the above. Labeled oligomers are selected for ligation to a probe/primer such that the resulting extended primer is a labeled mutation-specific polynucleotide.

Figure 4:
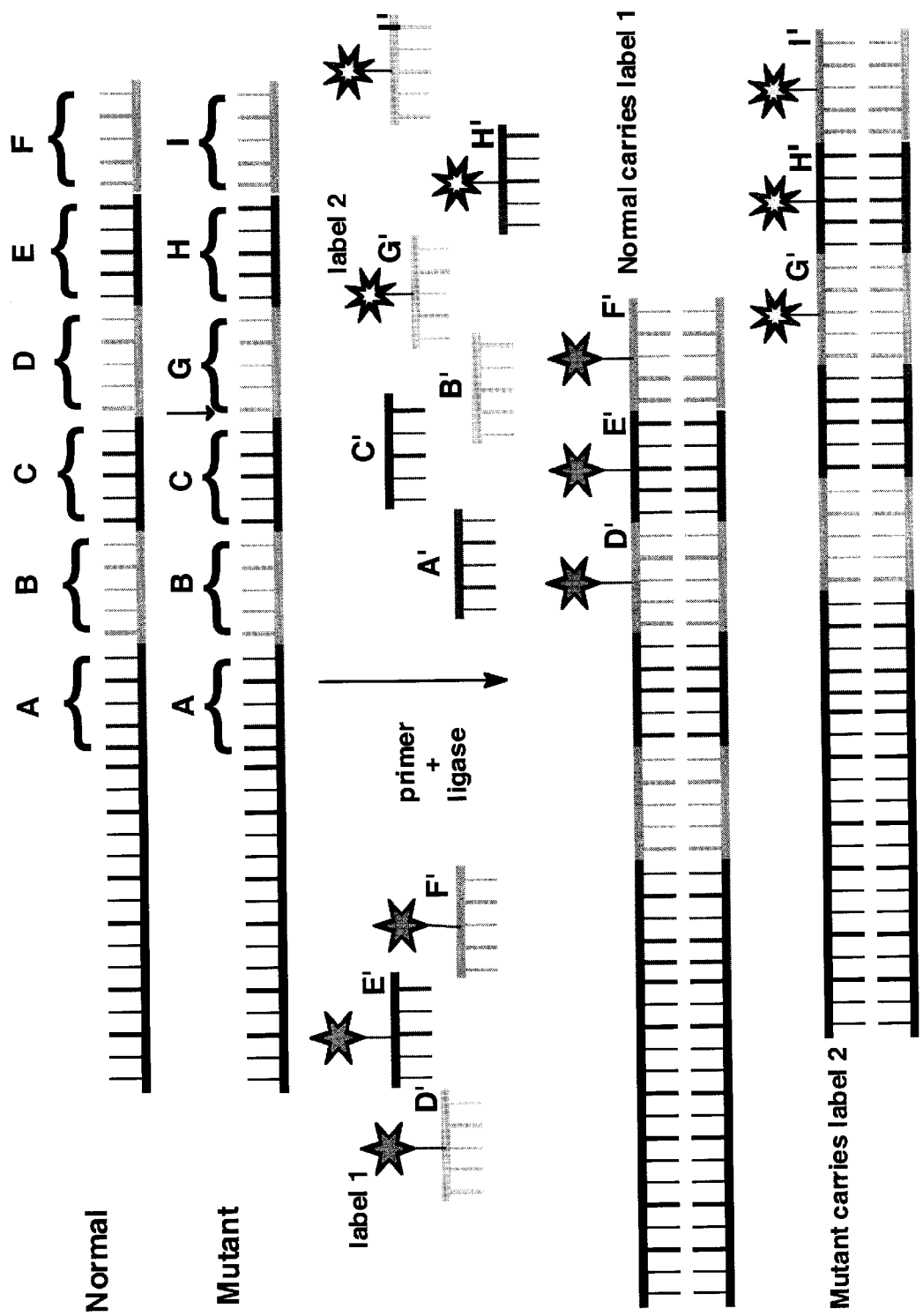
FIG. 4 schematically depicts a method for detecting two different genotypes of a mutation in a gene by the ligation of different sets of detectably labeled mutation specific or wild-type specific oligomers onto a template-bound primer. The mutation specific oligomers bear a first label while the wild-type specific oligomers bear a second label.

The methods of the present invention can be used to provide a method for the differentiation of heterozygotes from homozygotes for such a genetic condition. Since two copies of a chromosome containing a DNA sequence of interest are present in a sample, the method of synthesizing labeled complementary DNA provides a means for distinguishing heterozygotes from either homozygote. A set of oligomers carrying a first label which, when ligated, produce a portion of a strand complementary to the normal sequence is provided for ligation. Another set of oligomers carrying a second label produces a portion of a strand complementary to the mutant sequence upon ligation (FIG. 4). Ligating the sets of oligomers to a probe hybridized to target DNA in the sample creates a polynucleotide complementary to the sample genotype. The three genotypes are resolved by the determining which labels are present in the newly synthesized DNA. Homozygous DNA will contain one label or the other; heterozygous DNA will contain both.

When the sequence to be synthesized is not known, a library of a large number of the total possible pool of oligomers is used. The latter situation occurs in sequence analysis and mutation screening. When used in conjunction with the methods of ascertaining the base sequence of a newly synthesized polynucleotide described in detail below, numerous mutations of a particular gene can be analyzed and identified simultaneously. The ability to test for multiple mutations in a gene would enable screening for genetic diseases such as cystic fibrosis for which more than 500 mutations have been identified.

In yet another aspect, there is provided a method of synthesizing an immobilized single stranded nucleic acid having a region whose base sequence is complementary to a portion of the base sequence of a test nucleic acid comprising:

a) providing a capture probe/primer which is complementary to a portion of the test single stranded nucleic acid;

b) contacting the capture probe/primer with the test single stranded nucleic acid under hybridizing conditions to capture the test single stranded nucleic acid and form a captured probe-test nucleic acid hybrid having a single stranded region and a double stranded region;

c) contacting the captured hybrid with a plurality of oligonucleotide 5'-monophosphates;

d) ligating at least some of the plurality of oligonucleotide 5'-monophosphates to the capture probe/primer to extend the double stranded region;

e) removing the oligonucleotide 5'-monophosphates which are not ligated; and f) denaturing the captured probe-test nucleic acid hybrid having an extended double stranded region to remove the test nucleic acid from the solid support and produce the immobilized single stranded nucleic acid.

The method controls the point of origin and is not limited by the size of oligomers to be ligated. When the sequence to be transcribed is exactly known, the oligomers can be pre-selected to reduce cost and complexity.

Another aspect of the invention is a method of synthesizing multiply labeled nucleic acid where the extent of label incorporation is controlled and provides a high density of labeling. When using an immobilized primer to serve the dual purpose of capture probe and primer the process comprises: a method of synthesizing an immobilized multiply labeled single stranded nucleic acid comprising:

a) providing a capture probe/primer which is complementary to a portion of the test single stranded nucleic acid;

b) contacting the capture probe/primer with the test single stranded nucleic acid under hybridizing conditions to capture the test single stranded nucleic acid and form a captured probe-test nucleic acid hybrid having a single stranded region and a double stranded region;

c) contacting the captured hybrid with a plurality of labeled oligonucleotide 5'-monophosphates;

d) ligating at least some of the plurality of labeled oligonucleotide 5'-monophosphates to the capture probe/primer to form a captured probe-test nucleic acid hybrid having an extended double stranded region;

e) removing the labeled oligonucleotide 5'-monophosphates which are not ligated; and f) denaturing the captured probe-test nucleic acid hybrid having an extended double stranded region to remove the test nucleic acid from the solid support and produce an immobilized labeled single stranded nucleic acid containing a plurality of labels.

The primer can alternatively be a nonimmobilized primer for the purposes of synthesizing a multiply labeled nucleic acid. This embodiment comprises:

a) providing a primer which is complementary to a portion of a test single stranded nucleic acid;

b) contacting the primer with the test single stranded nucleic acid under hybridizing conditions to form a primer-test nucleic acid hybrid having a single stranded region and a double stranded region;

c) contacting the hybrid with a plurality of labeled oligonucleotide 5'-monophosphates;

d) ligating at least some of the plurality of labeled oligonucleotide 5'-monophosphates to the primer to form an extended primer-test nucleic acid hybrid having an extended double stranded region; and e) removing the labeled oligonucleotide 5'-monophosphates which are not ligated.

The method can further comprise the step of separating the extended primer strand from the template nucleic acid strand if desired. The label borne on each oligonucleotide 5'-monophosphate can be different or all can be the same label. Alternatively, a limited number of different labels, e.g. 2–5 labels, can be employed. The choice of labels used will be governed by the final application.

The present methods, in contrast to other methods of labeling nucleic acids described in the Background section, can prepare virtually any length nucleic acid, but would probably be most useful for products of at least about 50 bases. Shorter products would have less labels attached. One of the main advantages is that the degree and position of label attachment is precisely controlled. For example, pentamers bearing one label each lead to product in which every fifth base is labeled, providing a label density of 20%. Still higher densities can be achieved with shorter oligomers or with pentamers bearing two or more labels each.

The ability to controllably label at these high densities will be particularly advantageous in diagnostic tests where detection sensitivity is paramount. Higher label densities should translate to improved limits of detection. Controlled labeling will contribute to improved assay precision. The labels can be virtually detectable species, including radioisotopes, chemiluminescent labels and fluorescent labels, calorimetric labels detected on the basis of absorption of light, specific binding molecules including antigens and antibodies, binding proteins such as streptavidin and haptens such as biotin and digoxigenin. In addition, when the label is a small hapten, the detectable label can be a species such as an enzyme which is bound to the nucleic acid via an enzyme-anti-hapten conjugate. In the latter regard, the use of pentamer ligation to produce labeled nucleic acid provides still another advantage. The bulky enzyme labels would be attached at every fifth base, which places them at nearly 180° angles along the double helix from the nearest neighboring label. Consideration of the internucleotide separation and molecular diameters of enzymes, reveals that even relatively large globular proteins can be accommodated at this labeling density without severe steric congestion.

Figure 5:
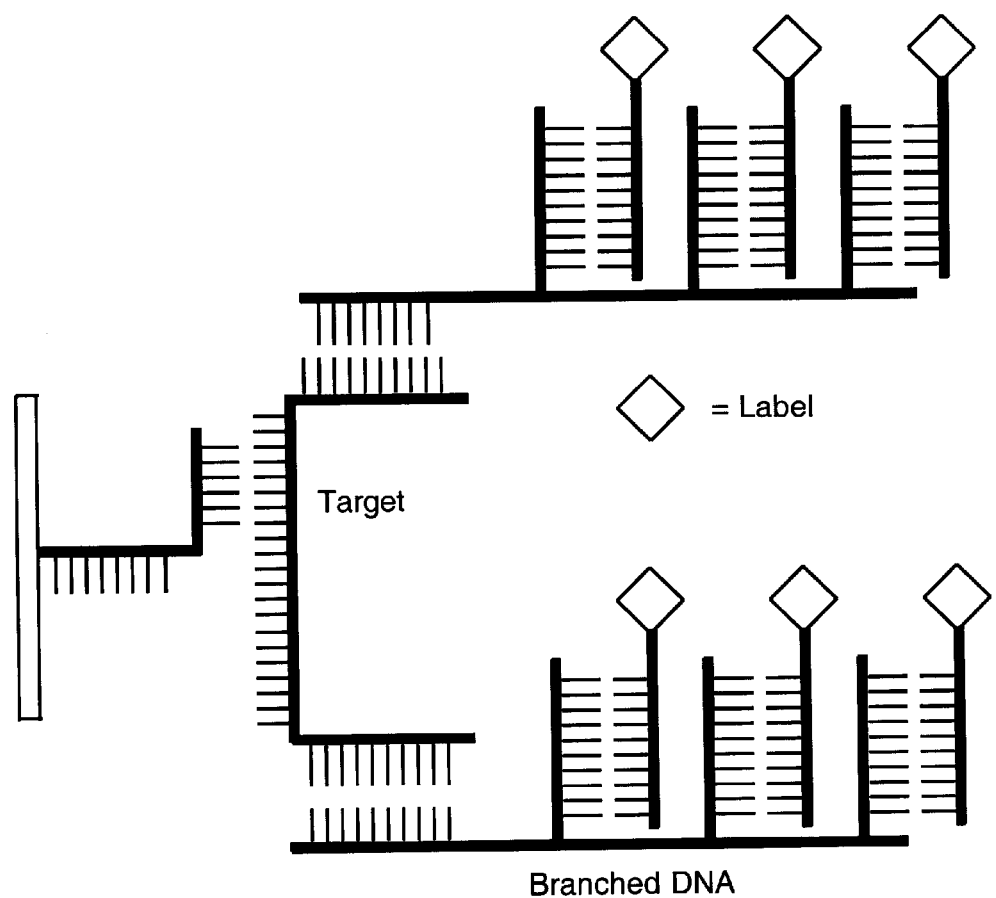
FIG. 5 depicts an example of branched DNA or amplification multimers.
Figure 6:
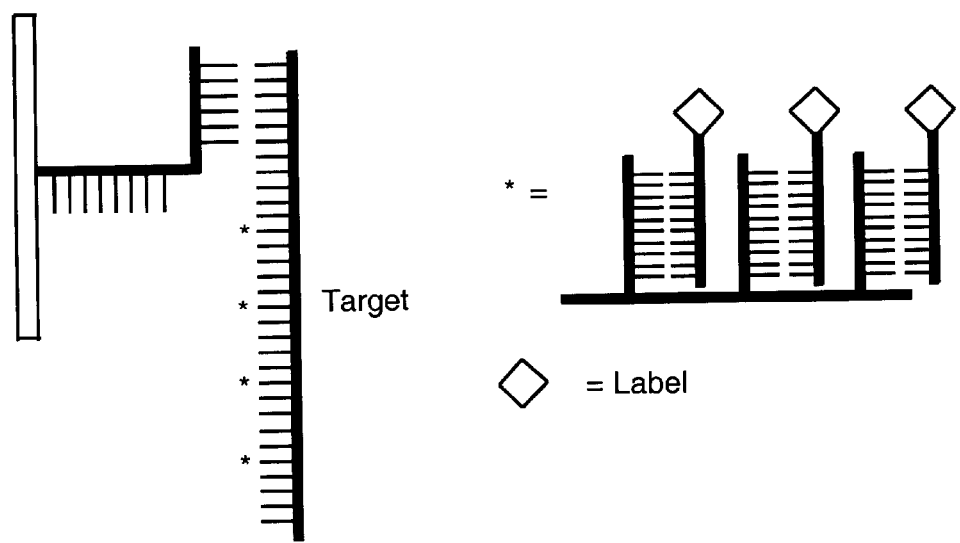
FIG. 6 depicts an adaptation of branched DNA in which at least the first branch is prepared by ligation of labeled oligomers for providing branch points at regularly spaced intervals.

Still higher label densities can be achieved by adopting the branching label principle in conjunction with the incorporation of regular labeled oligomers as depicted in FIGS. 5 and 6. In practice, some or all of the oligomers would constitute a "handle" such as a hapten or short recognition sequence which is used to bind to a branched amplification multimer.

Alternately, the arms of the branches could be prepared by the ligation of labeled short oligomers, so that each of the multiple arms carries detectable labels. Synthesis of densely labeled nucleic acids by ligation of labeled oligomers can be adapted to other types of branching DNA technology such as the DNA dendrimers (Polyprobe, Philadelphia).

The oligonucleotide 5'-phosphates used in the above-disclosed methods of synthesis, amplification, preparing labeled polynucleotides or immobilized polynucleotides are preferably relatively short. In these applications, it is not necessary to use a substantial fraction of the total library of oligomers of a given length in order to be able to synthesize the desired nucleic acid of known sequence. The size of the oligomers can take any convenient value, typically from 2 to about 20 bases. When high density labeling is desired, it is preferred that the oligomers contain less than about 10 bases and preferably from about 4 to about 8 bases.

In another aspect of the invention, methods are provided for determining the sequence (sequencing) of an unknown single stranded nucleic acid. The method can be applied to RNA, ssDNA and denatured dsDNA sequences of suitable lengths provided that at least a portion of the sequence is known. The latter restriction is necessary in order that a capture probe/primer may be designed.

The capture probe/primer is immobilized or capable of being immobilized onto a solid support such as a bead, tube, filter, membrane microtiter plate or chip. The capture probe should be of sufficient base length to guarantee efficient hybridization and represent a unique partial sequence on the test nucleic acid. These conditions will generally be satisfied with a length of at least 10 bases and preferably at least 15 bases. The capture probe can be immobilized onto the solid support in any art-recognized way. A commonly used means is to provide a biotin label for binding to a streptavidin-coated support. Streptavidin-coated beads and microtiter plates are commercially available.

The oligonucleotide 5'-phosphates used in sequence analysis determinations performed in accordance with the methods disclosed herein are preferably relatively short. It is necessary to use a substantial fraction of all possible oligomers of a given length in order to be able to synthesize long stretches of nucleic acid of unknown sequence. In order to keep the total library size manageable, it is desirable to limit the size of the oligomer to less than about 8 bases. It is more preferred that the oligomers contain 5 or 6 bases. A further requirement in embodiments involving sequence analysis is that all oligonucleotide 5'-phosphates be of the same number of bases.

In this aspect of the invention, a method for determining the sequence of a portion of a single stranded nucleic acid comprises the steps of:

a) providing a capture probe/primer which is complementary to a portion of the single stranded nucleic acid;

b) hybridizing the capture probe/primer with the single stranded nucleic acid to capture the single stranded nucleic acid and form a captured probe-nucleic acid hybrid having a single stranded region and a double stranded region;

c) contacting the captured hybrid with a plurality of labeled oligonucleotide 5'-monophosphates of the same number of bases each oligonucleotide 5'-monophosphate having a unique label;

d) ligating at least some of the plurality of labeled oligonucleotide 5'-monophosphates to the capture probe/primer to form a captured probe-nucleic acid hybrid having an extended double stranded region;

e) removing the labeled oligonucleotide 5'-monophosphates which are not ligated;

f) denaturing the captured probe-nucleic acid hybrid having an extended double stranded region to remove the nucleic acid from the solid support and produce an immobilized complementary single stranded nucleic acid containing a plurality of labels and a region whose sequence is complementary to a region of the nucleic acid;

g) detecting the plurality of labels;

h) relating the plurality of detected labels to the identity of their corresponding oligonucleotide 5'-monophosphates; and i) determining the base sequence of the portion of the nucleic acid from the identity of the plurality of oligonucleotide 5'-monophosphates.

The process of converting the collection of partial base sequences derived from the plurality of detected labels involves performing a set of analyses to relate the collection of partial base sequences to their correct relative order or position in the total sequence to be determined. A subset of partial base sequences is identified in the initial ligation experiment. The order of occurrence of each partial sequence in the full sequence is then deduced from a set of experiments in which one oligomer representing one partial sequence is excluded from the set of all identified partial sequences. For a nucleic acid sequence of N bases, the number of identified partial sequences of n bases would be N/n, assuming no duplicates. The number of such sets, each containing (N/n)−1 oligomers and lacking a different oligomer, equals the number of partial sequences, N/n. The ligation reaction of these sets to the hybridized primer produces a collection of extended primers of different lengths, ranging from 0 to N/n additional sets of n bases plus the length of the primer, i.e. primer+n, +2n, +3n, etc. Since the identity (sequence) of the excluded oligomer is known for each experiment, its relative position in the total sequence is given by the formula: 1+number of additional n-base units which were incorporated in that experiment.

Figure 7:
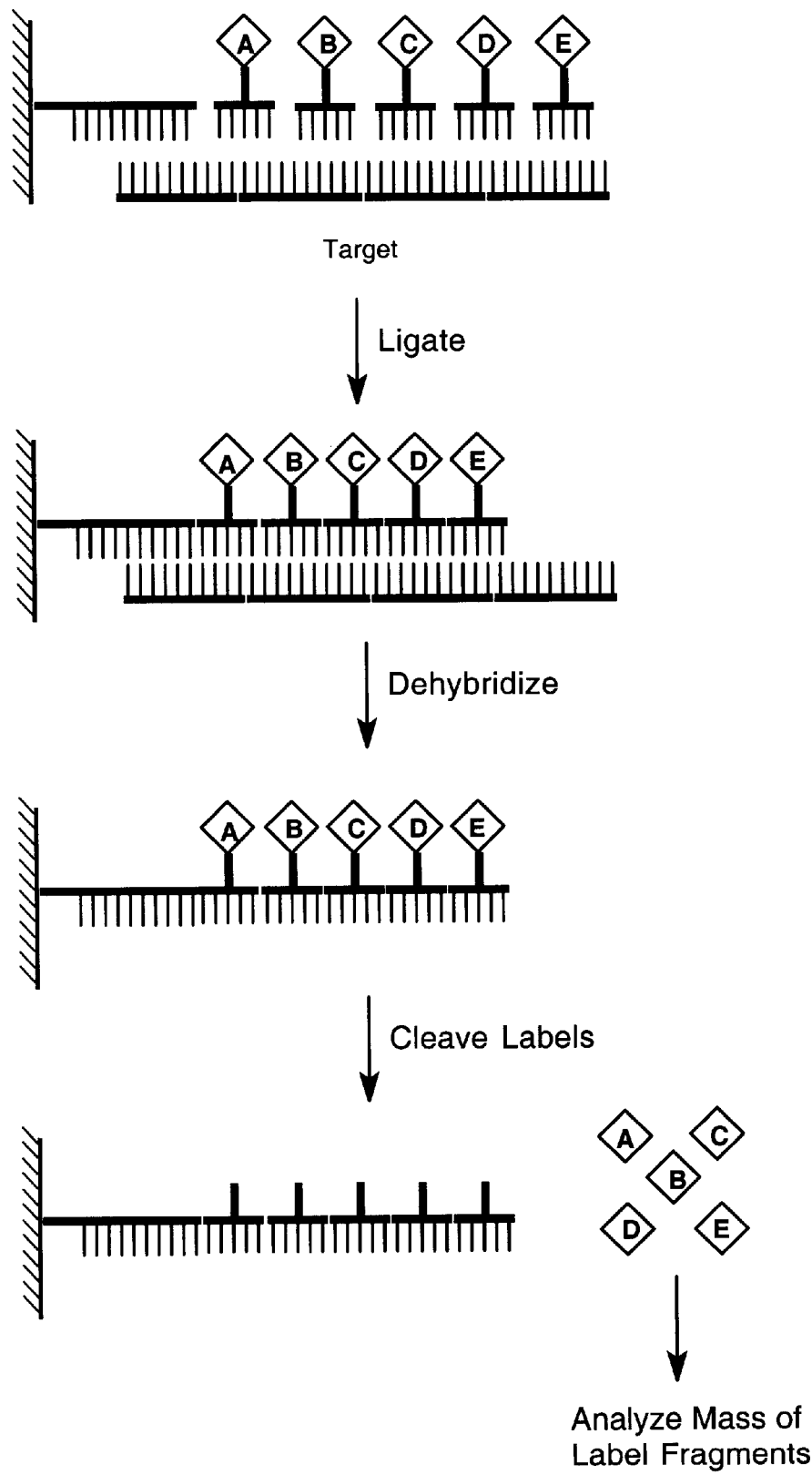
FIG. 7 schematically depicts a method for determining the sequence of a nucleic acid by the ligation of unique labeled oligomers onto a template-bound primer, cleaving the labels and analysis of the mass of each unique label.

There are several ways in which the reaction product of each of the aforementioned N/n experiments can be identified. Each method constitutes a different embodiment of the invention. In one embodiment, unique cleavable labels are provided on each oligomer. The plurality of unique labels is cleaved from the extended probe/primer to produce a set of label fragments, each having a unique molecular mass. This method of sequence analysis is depicted schematically in FIG. 7. The set of label fragments is analyzed by introduction into a mass spectrometer. In a preferred mode, the mass analysis is performed under conditions where the parent ion of each label fragment can be detected. The experimental output of each experiment consists of a set of molecular masses, each set containing a different number of values. The collection of sets of molecular masses is compared to determine the relative position of each unique label and its associated partial base sequence in the total sequence being determined. This analysis is most conveniently done by a computer algorithm.

The cleavable labels can be any molecular fragment capable of being controllably released from the extended probe/primer. Preferred labels are small organic molecules of molecular mass less than about 50,000 amu. It is desirable that the labels all be of one structural type, having a common functional group so that all are cleavable by a common means. One means for effecting cleavage is by thermolysis of a thermally labile group. A preferred thermally labile group for use in cleavable labels is a 1,2-dioxetane. It is well known that 1,2-dioxetanes undergo a thermal fragmentation of the dioxetane ring to produce two carbonyl fragments. Dioxetane-labeled oligomers can be prepared which release a carbonyl compound when heated by tethering a dioxetane group to a ribonucleotide or deoxyribonucleotide.

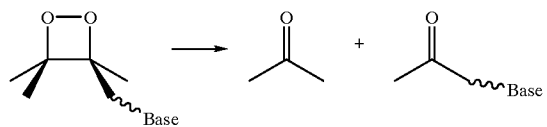

A library of oligomers would comprise the set of all possible sequences of n bases, each covalently attached to a unique dioxetane moiety. For convenience of synthesis, the linking functionality connecting the dioxetane ring group to the oligomer should be common to all members of the family of labeled oligomers. Substituents on the dioxetane ring at the carbon which is cleaved will vary among the members of the set of compounds.

Other thermally cleavable functional groups such as non-cyclic peroxides are known and can be used. The temperature required for thermolysis must be low enough so that oligonucleotide fragmentation does not occur.

The means of cleaving the cleavable label is not limited to thermal cleavage. Any means of controllably releasing the label from the extended probe/primer can be employed. Other means include, without limitation, enzymatic reactions, chemical reactions including nucleophilic displacements such as fluoride-induced silyl ether cleavage, basic or acidic hydrolytic fragmentations such as ester hydrolysis or vinyl ether hydrolysis, photochemical fragmentations, reductive cleavage such as metal-induced reductive cleavage of a disulfide or peroxide, oxidative cleavage of alkenes or diols.

An exemplary enzymatic reaction for label cleavage utilizes enzymatically triggerable dioxetanes as labels. Enzymatic deprotection of a protected phenolic substituent triggers cleavage of the dioxetane ring into two carbonyl compounds as depicted above. The reaction can be performed at room temperature and the rate of cleavage controlled by the amount and nature of the triggering enzyme and the characteristics of the reaction solution, e.g. pH. Numerous triggerable dioxetane structures are well known in the art and have been the subject of numerous patents. The spiroadamantyl-stabilized dioxetanes disclosed in U.S. Pat. No. 5,707,559 are one example, others containing alkyl or cycloalkyl substituents as disclosed in U.S. Pat. No. 5,578,253 would also be suitable. A linking substituent from the aforementioned spiroadamantyl, alkyl or cycloalkyl groups would be required to attach the dioxetane label to the oligomer. Linkable dioxetanes are disclosed in U.S. Pat. No. 5,770,743.

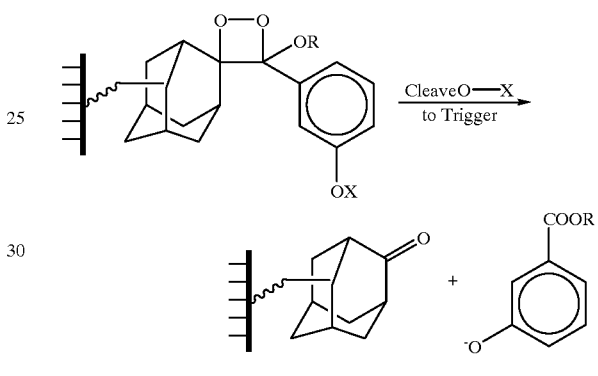

Chemical methods of cleaving triggerable dioxetanes are also well known and would be similarly useful in the methods of the invention. In the example above, X can be a trialkylsilyl group and the triggering agent fluoride. Other triggering agent/cleavable group pairs are described in, for example, the aforementioned 5,707,559, 5,578,253 and 5,770,743 patents.

The foregoing method comprised the steps of:
1) performing an initial ligation experiment with labeled oligomers,
2) releasing the labels, 3) detecting the labels, 4) determining the set of partial base sequences associated with the labels, 5) performing a set of ligation reactions with a subset of oligomers identified in the preliminary analysis to relate the collection of partial base sequences to their correct relative order or position in the total sequence. Alternatively, the preliminary ligation and analysis can be omitted and the sequence can be determined by performing sets of ligation reactions, excluding one oligomer in each set. In this mode, the sets would need to comprise the whole library of partial sequences less the excluded one. Detection and/or quantitation of the labels is then performed in the same manner as described above.

In the foregoing methods where arrays are prepared lacking one oligomer from the set of oligomers, an alternative approach would be to incorporate nonextendable oligomers for the particular oligomer which would otherwise be excluded. The nonextendable oligomer can be labeled or unlabeled, depending on the need. Such nonextendable oligomers could have a dideoxy base at the 3'-end of the oligomer so that there is no 3'-OH for ligation. The 3'-OH could be blocked, for example with a methyl group or a phosphate group, to prevent subsequent ligation. Modifications to the terminal base which prevent ligation are another possibility.

In another aspect, the method of ligating oligomers onto a template-bound primer for the purpose of sequence analysis can be performed using a single label with quantitative analysis. The process of determining the sequence can be achieved by performing a set of ligation reactions each reaction containing the full library of oligomers of n bases less one as described generally above. Each oligomer carries the same detectable label. Each ligation reaction produces an extended primer of a length, ranging from 0 to N/n additional sets of n bases plus the length of the primer, i.e. primer+n, +2n, +3n, etc. The quantity of detectable label in each reaction is proportional to the number of ligated oligomers. Collectively the set of extended primers produces all values from 0 to N/n with the maximum value resulting in all reactions in which the excluded oligomer is not present in the template sequence. The value of 0 occurs when the excluded oligomer represents the first five bases in the template sequence. Since the identity (sequence) of the excluded oligomer is known for each experiment, its relative position in the total sequence is given by the formula: 1+number of additional n-base units which were incorporated in that experiment. The template sequence is then deduced from the order of occurrence of each partial sequence (oligomer).

There are several ways in which the label can be detected. Each method or type of label constitutes a different embodiment of the invention. In one embodiment, the label is a fluorescent molecule such as the fluorescers FAM, JOE, ROX and TAMRA commonly used in automated dideoxy sequencing. Numerous methods of labeling nucleotides and oligonucleotides are known in the art and include direct attachment of label (Haugland, Handbook of Fluorescent Probes and Research Chemicals, (Molecular Probes, Eugene, Ore.), 1992). Labeling can also be accomplished by indirect means where, for example, where a universal linker such as biotin is provided as the primary label and a fluorescer-labeled binding partner for biotin provides the label.

In another embodiment, the label is a chemiluminescent compound and the quantity of label is detected by the light intensity produced by triggering the generation of chemiluminescence from the label. Several types of chemiluminescent compounds are known and can be used as labels. Representative examples include acridinium esters and sulfonamides, luminol or isoluminol derivatives, and dioxetanes (R. Handley, H. Akhavan-Tafti, A. P. Schaap, *J. Clin. Ligand Assay,* 20(4) 302–312 (1997)). A preferred chemiluminescent label is an acridan phosphate compound as disclosed in Applicant's co-pending application Ser. No. 09/099,656. The latter compounds are used advantageously because of their stability, high chemiluminescence quantum efficiency, ease of conjugation and ability to be triggered under a wide range of conditions, including in electrophoresis gels. Bioluminescent and electrochemiluminescent compounds are considered within the scope of detectable chemiluminescent labels.

In another embodiment, the label is a chromogenic compound and the quantity of label is detected by light absorbance. Another label type is a radioisotope such as $^{32}P$ and $^{35}S$ whose presence can be detected using scintillation counting or x-ray imaging. The label can also be an enzyme such as alkaline phosphatase, β-galactosidase, luciferase and horseradish peroxidase. The quantity of enzyme is determined by measuring the action of the enzyme on a fluorogenic, chromogenic or chemiluminogenic substrate.

The quantitative detection techniques described above rely on the ability to discriminate signal from 0 to N/n with unit resolution where N is the total number of bases to be sequenced and n is the number of bases in the oligomer phosphates used. The resolution demand of the detection process can be relaxed by performing m parallel sets of reactions where only a predetermined fraction(1/m) of the oligomers are labeled. If m sets of experiments are then performed in which a different portion of the library (N/m) is labeled in each set and the rest unlabeled, ligation of the library and detection produces a set of values in the range 0 to N/5 m in each set of experiments. The sum of the information in the m sets combines to produce the same information (total sequence). This reduces the measurement precision requirement and provides m-fold redundancy of results. As an example using pentameric oligomers, pentamers arbitrarily designated 1–205 would be labeled and the rest unlabeled in the first set. Numbers 206–410 would be labeled in a second set, numbers 411–615 in a third, 616–820 in a fourth and 821–1024 in a fifth set. Each of the five sets of ligations will produce data with numeric values from 0 to N/5 m. The individual reactions responsible for producing these values will differ among the five sets.

In still a further embodiment, unlabeled oligomers can be used in a method for sequencing by ligation when applied to polynucleotides of up to a few hundred bases. Methods of DNA sequence analysis using MALDI-TOF mass spectrometry have been developed to accurately determine the molecular mass of a series of polynucleotides differing in length by one base generated by exonuclease digestion of a nucleic acid. The technique is easily capable of discriminating polynucleotides differing in length by 5 bases on the basis of molecular mass. Current technology can accurately identify polynucleotides up to about 80–100 bases with adequate (single base) mass resolution. A series of ligated polynucleotide products formed in accordance with the methods of the present invention containing from 0 to about 100 ligated short oligonucleotides, such as pentamers, would require no better instrumental resolution and would extend the mass range which could be sequenced several fold.

Another aspect of the invention comprises a method of detecting a target nucleic acid by detecting a labeled extended nucleic acid which is complementary to the target, the method being a simpler alternative than traditional Southern and northern blotting. Preparation of the labeled extended complementary nucleic acid is performed by ligation of a plurality of labeled short oligomers onto a probe/primer which is hybridized to the target. Extension is followed by denaturing electrophoretic separation and detection of the labeled species. The presence of the labeled extended primer is indicative of the presence of the target since ligation only takes place when the primer is hybridized to the target. It is preferred that the label is detectable in the gel. Suitable labels include acridan alkenes as described in U.S. Patent application Ser. No. 09/099,656 filed on Jun. 17, 1998, which can be detected by chemiluminescence, and fluorescers which are readily detectable in gels. In this embodiment, no blotting is performed. If the label is such that detection in the gel is not feasible, then blotting onto membrane is performed and then detection of the label is performed on the membrane. In no case is hybridization on the membrane, antibody binding, enzyme-conjugate binding, substrate addition or other commonly used methods necessary.

In an alternate embodiment of this method, the labeled extended complementary nucleic acid remains hybridized to the target and after electrophoresis, the band detected at the appropriate molecular weight in the manner described above. This mode may be desirable when accurate molecular weight information is needed. In this method it is more convenient to provide substantially the full library of possible oligomer 5'-phosphates of n bases when the target is much longer than the probe/primer. In cases where the target sequence is known and where its length makes it more practical, it may be preferred to preselect the subset of oligonucleotide 5'-phosphates.

Yet another embodiment comprises providing a suitable fluorescent donor as a label on a probe/primer and a suitable fluorescent acceptor as a label on the oligomers. It is not necessary to label each oligomer. Ligation is performed on hybridized primer to form an extended primer bearing a fluorescent donor and one or more fluorescent acceptor labels. Under suitable conditions, i.e. when the donor and acceptor possess sufficient spectral overlap for energy transfer to be feasible and the spatial separation between donor and acceptors are within the Förster distance, energy transfer between fluorescers can occur within the extended primer. Irradiation of the extended primer at a wavelength absorbed by the fluorescent donor on the primer results in fluorescence from the acceptor on the extended portion. This method can therefore serve as the basis for a homogeneous assay for detecting a target nucleic acid since the presence of target is required to permit the ligation to occur and thereby bring the fluorophores within energy transfer distance.

Another method for detecting a target nucleic acid based on the ligation of a plurality of labeled oligomers comprises using a fluorescent intercalating dye as a label. It is known that certain dyes become fluorescent when intercalated within the double helix of double stranded nucleic acids. An example is the widely used compound ethidium bromide. Accordingly, a method for detecting a target nucleic acid comprises:

a) providing plurality of oligonucleotide 5'-phosphates wherein at least some contain a fluorescent intercalating dye as a label;

b) providing an oligonucleotide primer which is complementary to a portion of a target nucleic acid;

c) contacting the primer with the target nucleic acid under hybridizing conditions to form a primer-target duplex having a single stranded region and a double stranded region;

c) contacting the duplex with the plurality of oligonucleotide 5'-monophosphates;

d) ligating at least some of the plurality of oligonucleotide 5'-monophosphates to the duplex to extend the double stranded region;

e) detecting fluorescence from the intercalated bound label.

As an optional step, agarose can be added to the reaction to enhance fluorescence. In the absence of target, ligation does not occur, so the detection of fluorescence is evidence of the presence of the target and additionally is evidence that the primer was sufficiently complementary to the target to hybridize. The collection of oligomers can be the full library of all possible sequences, or a subset containing preselected members if the target sequence is known.

The fraction of labeled oligomers to use can be selected empirically with regard to the desired degree of detection sensitivity by using a range of different label densities. It may be desirable, depending on the size of the oligonucleotide 5'-phosphates, to limit the fraction of labeled oligomers to avoid self quenching of fluorescence.

Another aspect of the present invention comprises a library of short oligonucleotide 5'-phosphates. It is preferred that the oligonucleotides consist of 5 bases or less, with pentamers being more preferred. The number of pentamers required for the full library is $4^5$ or 1024 individual compounds.

In practice it may not be necessary to include all oligonucleotide 5-phosphates of length n in forming a library. In applications where the number of oligonucleotides required to produce the given sequence of N nucleotides is small compared to the total number of oligonucleotides in the library ($N/n<<4^n$), partial libraries will often suffice to maintain a high probability of providing all of the required oligonucleotides. As an illustration of this point, a polynucleotide of 500 bases consists of 100 pentameric units. The full library of all pentamers contains 1024 compounds, a more than 10-fold excess.

It may be desirable to use a partial library which excludes selected sequence oligonucleotides which hybridize too weakly or strongly. In several methods described above for sequence analysis of a test nucleic acid, the library will be predetermined to consist of a selected number, x, of oligomers determined in a proceeding step from the identification of x+1 labels. In the sequencing method, a collection of partial libraries of x bases each will be used. Each partial library will lack a different one of the x+1 oligomers identified on the basis of the preceding step.

The partial libraries can be preformed by preparing all of the possible combinations of x oligomers beforehand. Alternatively, the partial libraries can be assembled as needed from the individual oligomers. The assembly of such partial libraries can be accomplished by robotic workstations with automatic fluid handling capabilities.

In general, the library of oligonucleotide 5'-monophosphates will contain labeled oligonucleotide 5'-monophosphates, in particular those bearing detectable labels. In some uses, all of the members of the library will bear a detectable label. In other applications, a preselected fraction of the members will be labeled. An example is the method of quantitative analysis disclosed above where, for example, five libraries of all possible oligomers are formed, each library having a different one-fifth fraction of the members being labeled.

In another embodiment of a library, at least one of the constituents of a library is a nonextendable oligomer. The nonextendable oligomer can be labeled or unlabeled. Such nonextendable oligomers could have a dideoxy base at the 3-end of the oligomer so that there is no 3'-OH for ligation. The 3'-OH could be blocked, for example with a methyl group or a phosphate group, to prevent subsequent ligation. Modifications to the terminal base which prevent ligation are another possibility.

Synthesis of oligomers—Oligonucleotides are readily synthesized using standard methods of synthesis well known to those of skill in the art including, e.g., phosphoramidate chemistry. Phosphorylation of oligonucleotides is performed using a polynucleotide kinase and ATP or by chemical methods of phosphorylation as described in (L. A. Slotin, *Synthesis,* 737–752 (1977); T. Horn, M. Urdea, *Tetrahedon Lett.,* 27, 4705–4708 (1986)). A kit is commercially available for carrying out 5'-phosphorylation (Phosphate-ON, Clontech, Palo Alto, Calif.).

Methods for the automated synthesis of oligonucleotides are well known in the art and in common commercial use. A common method uses a solid support of immobilization and automated reagent handling to add nucleotides sequentially. All addition, blocking and deblocking steps are under computer control. Such instruments are available from several commercial suppliers such as Applied Biosystems, CA (Model 392 and 394). Automated instruments for transfer of liquid reagents and samples can be performed under computer control using laboratory robots such as are commercially available (Perkin-Elmer, model 800 Catalyst, Beckman Instruments Biomek). Newer techniques for the high speed synthesis or synthesis of large numbers of oligonucleotides utilize photolithographic techniques or ink jet technology for the rapid and precise delivery of reagents and reactants.

Still a further aspect of the invention comprises annealing a primer oligonucleotide 5=-phosphate to a single-stranded template and, in the manner disclosed above, ligating a library of oligomers to extend the primer from both ends to duplicate the template strand. The method is useful in a method to render a single stranded template double stranded in order to clone it. This would find utility in methods for isolating related genes or gene families.

In an exemplary method, a primer oligonucleotide is hybridized to a template strand in the presence of a library of all possible combinations of pentamers, a DNA ligase, and an appropriate reaction buffer. Pentamers that are complementary to the template strand, and in exact register with the 5' and 3' ends of the primer oligonucleotide, anneal and are sequentially ligated by the action of the DNA ligase. The template strand thereby becomes substantially copied or rendered double-stranded. This procedure can be used to detect target templates in a mixture of nucleic acid strands and to prepare double-stranded nucleic acids for cloning using cloning vectors and techniques known in the art.

In order to more fully describe various aspects of the present invention, the following examples are presented which do not limit the scope of the invention in any way.

EXAMPLES

Example 1. General Procedure

The template used in this experiment was a PCR amplified product (200 bp) of exon 10 region of the cystic fibrosis transmembrane regulator (CFTR) gene. The PCR-amplified DNA of the CFTR gene was purified either by running it through a column (Qiaquick PCR purification kit, Qiagen, Santa Clarita, Calif.) or by ethanol precipitation. The DNA was resuspended in distilled water at a concentration of approximately 0.5 $\mu g/\mu L$. Pentamers bearing a 5'-phosphate group and primers were obtained commercially (Oligos Etc., Wilsonville, Ore.).

The primer and pentamers were designed to be complimentary to either the sense or the antisense strand of the template used. The length of the primer used in these experiments ranged from 21 to 26 nucleotides. The pentamers were designed in such a way that the first pentamer anneals to the template immediately adjacent to the 3' end of the primer. The subsequent primers line up contiguously starting at the 3' end of the first pentamer. Hybridization of the primer and pentamers to the template followed by ligation by T4 DNA ligase results in back to back ligation at the 5'–3' junctions. To enable the detection of the ligated primer-pentamer products, biotin-dUTP labeled pentamers (at the internal dTTP position) were used.

Hybridization of the primer and pentamers to the template and their ligation to each other was accomplished in a 3-step process. First, the template-primer-pentamer mix was heated to 94° C. and kept for 5 min to allow the denaturation of the double stranded template. The mix was cooled to 60° C. or 65° C., depending on the size and base composition of the primer, to anneal the primer to the template for 2 min. Finally, the reaction tubes were cooled to 16° C. After about 2 min at 16° C., ligation buffer (66 mM Tris HCl, pH 7.6, 6.6 mM $MgCl_2$, 10 mM DTT, 66 $\mu M$ ATP, Amersham) and T4 DNA ligase, 1 U (Amersham, 1:10 dilution) were added and ligated at 16° C. for 2 hours. The ligation reaction was stopped by adding 1/10th volume of loading dye (0.01% xylene cyanol and 0.01% bromophenol blue, and 0.01M EDTA in deionized formamide).

The ligation reactions were electrophoresed on a denaturing polyacrylamide gel along with biotin-labeled oligonucleotide size markers. The DNA was capillary transferred to a nylon membrane, bound with anti-biotin antibody-HRP conjugate, and detected by reacting with Lumigen PS-3 (a chemiluminescent HRP substrate) and exposing to an x-ray film. The size of the ligated product varies depending on the number of pentamers ligated to the primer.

Example 2. Determining Optimal Concentrations of Template, Primer and Pentamers.

Template: A 200 bp PCR product of CFTR exon 10 (See the attachment for the template DNA sequence) was obtained by PCR amplification using a set of sense (5' ACTTCACTTCTAATGATGATTATG 3') (Seq. ID #1) and an antisense (5= CTCTTCTAGTTGGCATGCTTTGAT 3') (Seq. ID #2) primers.

A 26 base oligonucleotide complementary to the sense strand of the template DNA was designed as a primer (5' AGTGGAAGAATTTCATTCTGTTCTCA 3') (Seq. ID #3).

Pentamers: Six 5-base long oligonucleotide 5'-phosphates complementary to the sense strand immediately adjacent the 3' end of the primer were prepared. The 5' end of the first pentamer aligns immediately next to the 3' end of the primer, the 5' end of the second pentamer aligns immediately next the 3' end of the first pentamer and so on. To facilitate ligation, the 5' end of each pentamer was phosphorylated. To enable the detection of the ligation products, pentamers 1 and 3 were labeled with biotin-dUTP at the central dTTP position and the last pentamer was labeled with biotin at the 3' end. The pentamers were as follows:

Pentamer 1: 5' $PO_4$-GTTTT 3'
Pentamer 2: 5' $PO_4$-CCU*GG 3' U*=U-Biotin
Pentamer 3: 5' $PO_4$-ATTAT 3'
Pentamer 4: 5' $PO_4$-GCCU*G 3'
Pentamer 5: 5' $PO_4$-GCACC 3'
Pentamer 6: 5' $PO_4$-ATTAA 3'-Biotin.

Ligations were performed using T4 DNA ligase and ligation buffer (Amersham), according to the ligation conditions described in Example 1. The ligations were performed in a volume of 20 $\mu L$. The amount of template was kept constant at about 1 $\mu g$ per reaction. The amount of primer was varied from 100 ng to 1 pg between reactions. The amount of each pentamer was varied from 2 ng to 0.2 pg in each reaction. The reaction with 1 $\mu g$ of template, 100 ng of primer, and 2 ng of each pentamer contained approximately equimolar concentrations of the template, primer and pentamers. The primer and pentamers were varied systematically to determine the lowest amount of detectable ligation product.

The ligation reactions were electrophoresed, capillary transferred to a nylon membrane, bound with anti-biotin antibody-HRP conjugate, and detected with Lumigen PS-3 as described in Example 1. A full-length primer-pentamer ligation product of expected size (56 bp) was detected in the ligation reaction containing 100 ng of primer and 20 ng of each pentamer (0.6 $\mu M$). Lower concentrations of the primer and pentamers in the ligation reaction yielded very low amount or no detectable ligation product under these conditions.

Example 3. Ligations with varying number of pentamers.

To show that the pentamers are sequentially ligated to the primer starting from the first pentamer (immediately downstream from the primer), ligations were performed using the template, primer and pentamers of Example 2 by incrementing the number of pentamers in each reaction. All the reactions contained equimolar concentrations (0.6 µM) of the template, primer and each pentamer. The ligations were performed as described above and the products detected by binding with anti-biotin-HRP antibody and reacting with Lumigen PS-3 substrate.

As expected, the size of the ligation product increased incrementally by five bases with the addition of each pentamer starting from the first pentamer and so on. There was no ligation product in the absence of the first pentamer and with the rest of the pentamers in the reaction demonstrating the requirement of the primer and specificity of the pentamers for the ligation to occur. In one ligation reaction containing the first four pentamers, there were two bands of the ligated product one of which was the expected size and the other was the size expected when all five pentamers are present in the reaction. Comparing the sequences of the pentamers revealed a single base difference between the third and fifth pentamers. The third pentamer appears to hybridize at the fifth pentamer position when the fourth pentamer is present in the reaction.

| Reaction | Pentamers Used | Product Length |
|---|---|---|
| 1 | 2, 3, 4, 5, 6 | 26 (primer) |
| 2 | 1, 2 | 36 |
| 3 | 1, 2, 3 | 41 |
| 4 | 1, 2, 3, 4 | 46 |
| 5 | 1, 2, 3, 4, 5 | 51, 56 |
| 6 | 1, 2, 3, 4, 5, 6 | 56 |

In reaction 1, the product, which consisted of the primer alone, was detected by virtue of a label on the primer.

Example 4. Competition from "Out of Register" Pentamer Set.

This example demonstrates that the ligation of a set of pentamers to a primer in a contiguous chain starting from the 3' end of the primer is not affected by the presence of a second set of pentamers which are also complementary to the template and also align contiguously, but begin at a position 'one-base-out' from the 3' end of the primer. Both the correct pentamer sets (1–8) and one-base-out pentamer sets (1a–5a) were included in the reaction along with the template and primer during the denaturing, annealing at 60° C. and ligation steps. The ligation reactions contained equimolar (0.6 µM) concentrations of template, primer and each of the pentamers.

Primer (5' ATTAAGCACAGTGGAAGAATTTCAT 3') (Seq ID #4)
Pentamer 1: 5' PO$_4$-TCU*GT 3' Pentamer 1a: 5' PO$_4$-CTGTT 3'
Pentamer 2: 5' PO$_4$-TCTCA 3' Pentamer 2a: 5' PO$_4$-CTCAG 3'
Pentamer 3: 5' PO$_4$-GTTTU* 3' Pentamer 3a: 5' PO$_4$-TTTTC 3'
Pentamer 4: 5' PO$_4$-CCU*GG 3' Pentamer 4a: 5' PO$_4$-CTGGA 3'
Pentamer 5: 5' PO$_4$-ATTAT 3' Pentamer 5a: 5= PO$_4$-TTATG 3'
Pentamer 6: 5' PO$_4$-GCCU*G 3' Pentamer 6a: 5' PO$_4$-CCTGG 3'
Pentamer 7: 5' PO$_4$-GCACC 3'
Pentamer 8: 5' PO$_4$-ATTAA 3'-biotin The target region of the template comprises the sequence:
3' TAA TTC GTG TCA CCT TCT TAA AGT AAG ACA AGA GTC AAA AGG ACC TAA TAC GGA CCG TGG TAA TT 5' (Seq ID #5)

| Reaction | Pentamers Used | Product Length |
|---|---|---|
| 1 | 1, 1a–6a | 31 (primer + 5) |
| 2 | 1, 2, 1a–6a | 36 |
| 3 | 1–3, 1a–6a | 41 |
| 4 | 1–4, 1a–6a | 46 |
| 5 | 1–5, 1a–6a | 51 |
| 6 | 1–6, 1a–6a | 56 |
| 7 | 1–7, 1a–6a | 61 |
| 8 | 1–8, 1a–6a | 66 |
| 9 | 2–8, 1a | 26 (primer) |
| 10 | 1–8, 1a–6a (no primer) | none |

Even in the presence of a set of six competing pentamers, the ligation products formed were the result of ligation of the "correct" pentamers being ligated to the primer. Reaction 10 confirmed that the presence of primer is required for ligation to occur. The one-base-out pentamers did not appear to interfere with the ligation of the correct pentamers.

Example 5. Competition from Labeled "Out of Register" Pentamer.

The experiment as Example 4 but pentamer 1a was biotinylated. This afforded the opportunity to directly observe the formation of any ligation products from the set of pentamers 1a–6a. No ligation products were observed from the set of one-base-out pentamers.

Example 6. Ligation Experiments Using JH Downstream Template.

Primer-directed pentamer ligation products were also obtained using as the template a 700 bp DNA downstream of immunoglobulin heavy chain joining region (JH) cloned into a plasmid vector. The JH downstream region was amplified by PCR, cloned into a plasmid vector which was then digested with Eco RI to obtain a sufficient amount of the template DNA. The restriction digest was separated on an agarose gel, and the DNA band of interest extracted using a gel extraction kit (Qiagen). The DNA was resuspended in distilled water at a concentration of approximately 0.5 µg/µl.

The primer and pentamers used with this template are shown below:
21mer Primer: 5' GAAACCAGCTTCAAGGCACTG 3' (Seq. ID #6)
Pentamer 1: 5' Phosphate AGGU*C
Pentamer 2: 5' Phosphate CU*GGA 3'
Pentamer 3: 5' Phosphate GCCU*C 3'
Pentamer 4: 5' Phosphate CCU*AA 3'
Pentamer 5: 5' Phosphate GCCCC 3'-Biotin Ligations were performed with 500 ng of template, 100 ng of primer, and 20 ng of each pentamer in each 20 µL ligation reaction. The number of pentamers was incrementally increased in each successive ligation reaction to show that the size of the ligation product grew in 5 base increments with each addition of a pentamer.

After performing the ligation reactions according to the general method of Example 1, there was a 5-base incremental increase in the size of the ligation product with each addition of successive pentamers. There were two bands in the ligation reaction containing the first four pentamers, the upper band being more intense than the lower band. The size of the upper band was the same as when all five pentamers were used for the ligation. This is probably because there is sequence similarity between the third and fifth pentamers, so the third pentamer was ligated also at the fifth pentamer position.

Example 7. Ligation at Various Temperatures.

Ligations using the template, primer and the first four pentamers of Example 6 were performed at 30+ C., 37° C., 40° C. and 45° C. to examine the effect of ligation temperature on mismatch discrimination. The template, primer and pentamer concentrations were the same as in the previous experiment. Parallel reactions were performed and the relative amount of the four pentamer and five pentamer extension products assessed. At 30° C. ligation temperature, the correct size and the non-specific ligation products were of the same intensity. More of the correct size ligation product was detected at ligation temperatures of 37° C. and 40° C. At 45° C., the amount of correct size ligation product detected was diminished.

The foregoing description and examples are illustrative only and not to be considered as restrictive. It is recognized that modifications of the specific compounds and methods not specifically disclosed can be made without departing from the spirit and scope of the present invention. The scope of the invention is limited only by the appended claims.

What is claimed is:

1. A method comprising:
   a) providing a reaction mixture comprising a single stranded nucleic acid template, a primer having at least 15 bases which is complementary to a portion of the single stranded nucleic acid template and a plurality of oligonucleotide 5'-monophosphates wherein each oligonucleotide 5'-monophosphate consists of not more than 10 bases and wherein each of the oligonucleotide 5'-monophosphates is labeled;
   b) hybridizing the primer with the template under conditions which permit stable hybridization of the primer but not stable hybridization of the oligonucleotide 5'-monophosphates to form a primer-template hybrid having a single stranded region and a double stranded region;
   c) ligating more than one of the plurality of labeled oligonucleotide 5'-monophosphates in a contiguous manner onto the primer in one continuous process under conditions which permit stable hybridization of the primer but not stable hybridization of the oligonucleotide 5'-monophosphates to extend the double stranded region and synthesize a labeled complementary nucleic acid strand, wherein ligation of oligonucleotide 5'-monophosphates only occurs in the presence of the hybridized primer.

2. The method of claim 1 wherein each of the plurality of oligonucleotide 5'-monophosphates consists of 5 bases.

3. The method of claim 1 wherein each of the plurality of oligonucleotide 5'-monophosphates is of identical length.

4. The method of claim 1 wherein some of the plurality of oligonucleotide 5'-monophosphates contain a different number of bases from other of the plurality of oligonucleotide 5'-monophosphates.

5. The method of claim 1 wherein the ligation is performed by means of a ligase enzyme.

6. The method of claim 5 wherein the ligase enzyme is selected from T4 ligase, T7 ligase, Tth ligase, Taq ligase and *E. coli* DNA ligase.

7. The method of claim 5 wherein the ligase enzyme is T4 DNA ligase.

8. The method of claim 1 wherein the primer is immobilized onto a solid phase.

9. The method of claim 1 wherein the primer is in a solution.

10. The method of claim 1 further comprising separating the labeled complementary nucleic acid strand from the template.

11. The method of claim 1 wherein each labeled oligonucleotide 5'-monophosphate is labeled with the same label.

12. The method of claim 1 wherein each oligonucleotide 5'-monophosphate is labeled with a label that is specific for and identifies that oligonucleotide 5'-monophosphate.

13. The method of claim 1 wherein each oligonucleotide 5'-monophosphate contains 1 label.

14. The method of claim 1 wherein each label is a detectable label selected from radioisotopes, chemiluminescent labels, fluorescent labels, colorimetric labels and enzymes.

15. The method of claim 1 wherein each label is selected from binding proteins, antigens, antibodies, haptens and oligonucleotides.

16. The method of claim 1 further comprising the incorporation of at least one nonextendable oligomer the ligation of which terminates synthesis of the nucleic acid strand.

17. The method of claim 16 wherein each of the nonextendable oligomers is selected from oligomers which have a dideoxy base at the 3'-end, oligomers which have a blocked 3'-OH group at the 3'-end and oligomers which lack a phosphate group at the 5'-end.

18. The method of claim 1 wherein the synthesis of the labeled complementary nucleic acid strand synthesized in step c) is terminated at a predetermined position by excluding from the plurality of oligonucleotide 5'-monophosphates at least one oligonucleotide 5'-monophosphate which is complementary to the single stranded nucleic acid template and has a sequence necessary to extend the double stranded region.

19. The method of claim 1 wherein the synthesis of the strand of nucleic acid is unidirectional and proceeds by ligation to the 3' end of the primer.

20. The method of claim 1 wherein the primer contains a 5'-phosphate group and the synthesis of the strand of nucleic acid is unidirectional and proceeds by ligation to the 5' end of the primer.

21. The method of claim 1 wherein the primer contains a 5'-phosphate group and the synthesis of the strand of nucleic acid proceeds from both ends of the primer.

22. The method of claim 1 wherein the single stranded nucleic acid template has a segment of known sequence, wherein the primer is complementary to a portion of the segment of known sequence and wherein the plurality of labeled oligonucleotide 5'-monophosphates comprises a set of labeled oligonucleotide 5'-monophosphates selected to be complementary to a part of the segment of known sequence of the template adjacent to the portion of the segment of known sequence to which the primer is complementary.

23. A method for synthesizing a labeled double stranded nucleic acid wherein both strands are labeled comprising:

a) providing a reaction mixture comprising a double stranded nucleic acid template, a first primer which is complementary to a region of a first strand of the template, a second primer which is complementary to a region of a second strand of the template, wherein both primers have at least 15 bases, and a plurality of labeled oligonucleotide 5'-monophosphates wherein each oligonucleotide 5'-monophosphate consists of not more than 10 bases and wherein each oligonucleotide 5'-monophosphate is labeled;

b) separating the first and second strands of the double stranded nucleic acid;

c) hybridizing the first and second primers with the separated strands under conditions which permit stable hybridization of the primer but not stable hybridization of the oligonucleotide 5'-monophosphates to form first and second primer-template hybrids;

d) ligating more than one of the plurality of labeled oligonucleotide 5'-monophosphates in a contiguous manner onto each primer-template hybrid in one continuous process under conditions which permit stable hybridization of the primer but not stable hybridization of the oligonucleotide 5'-monophosphates to extend the first and second primers thereby producing double stranded nucleic acid, wherein ligation of oligonucleotide 5'-monophosphates only occurs in the presence of the hybridized primer; and e) repeating steps b–d at least once, thereby synthesizing a labeled double stranded nucleic acid wherein both strands are labeled.

* * * * *

```
                        SEQUENCE LISTING

<160> NUMBER OF SEQ ID NOS: 7

<210> SEQ ID NO 1
    <211> LENGTH: 24
    <212> TYPE: DNA
    <213> ORGANISM: primer

<400> SEQUENCE: 1
acttcacttc taatgatgat tatg                                       24

<210> SEQ ID NO 2
    <211> LENGTH: 24
    <212> TYPE: DNA
    <213> ORGANISM: primer

<400> SEQUENCE: 2
ctcttctagt tggcatgctt tgat                                       24

<210> SEQ ID NO 3
    <211> LENGTH: 26
    <212> TYPE: DNA
    <213> ORGANISM: primer

<400> SEQUENCE: 3
agtggaagaa tttcattctg ttctca                                     26

<210> SEQ ID NO 4
    <211> LENGTH: 25
    <212> TYPE: DNA
    <213> ORGANISM: primer

<400> SEQUENCE: 4
attaagcaca gtggaagaat ttcat                                      25

<210> SEQ ID NO 5
    <211> LENGTH: 65
    <212> TYPE: DNA
    <213> ORGANISM: DNA template

<400> SEQUENCE: 5
ttaatggtgc caggcataat ccaggaaaac tgagaacaga atgaaattct tccactgtgc    60
ttaat                                                            65

<210> SEQ ID NO 6
    <211> LENGTH: 21
    <212> TYPE: DNA
```

```
<213> ORGANISM: primer

<400> SEQUENCE: 6
gaaaccagct tcaaggcact g                                        21

<210> SEQ ID NO 7
<211> LENGTH: 21
<212> TYPE: DNA
<213> ORGANISM: primer

<400> SEQUENCE: 7
attcagtgcc atgggacata g                                        21
```